(12) United States Patent
Neumann

(10) Patent No.: US 12,068,066 B2
(45) Date of Patent: Aug. 20, 2024

(54) SYSTEM AND METHOD FOR GENERATING AN ADDICTION NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 291 days.

(21) Appl. No.: 17/188,008

(22) Filed: Mar. 1, 2021

(65) Prior Publication Data

US 2022/0277831 A1    Sep. 1, 2022

(51) Int. Cl.
*G16H 20/60*    (2018.01)
*A61B 5/00*    (2006.01)
(Continued)

(52) U.S. Cl.
CPC ............. *G16H 20/60* (2018.01); *G06Q 40/02* (2013.01); *G16H 10/60* (2018.01); *G16H 40/20* (2018.01);
(Continued)

(58) Field of Classification Search
CPC ........ G16H 20/60; G16H 70/60; G16H 40/20; G16H 10/60; G16H 50/70; G16H 50/20;
(Continued)

(56) References Cited

U.S. PATENT DOCUMENTS 7,187,790 B2    3/2007    Sabol
7,295,889 B2    11/2007    Lahteenmaki
(Continued)

FOREIGN PATENT DOCUMENTS

WO    2020069500 A1    4/2020

OTHER PUBLICATIONS

Koks et al., "Analysis of SNP profiles in patients with major depressive disorder," 2005, International Journal of Neuropsychopharmacology, pp. 1-8. (Year: 2005).*
(Continued)

*Primary Examiner* — Kenneth Bartley
(74) *Attorney, Agent, or Firm* — Caldwell Intellectual Property Law

(57) ABSTRACT

A system and method for generating an addiction nourishment program includes a computing device, the computing device configured to obtain an addiction element, produce an addiction signature as a function of the addiction element, wherein producing further comprises identifying a predictive signal as a function of an addiction directory, and producing the addiction signature as a function of the predictive signal and addiction element using a predictive machine-learning model, identify a physiological impact as a function of the addiction signature, wherein identifying a physiological impact further comprises receiving a medical influence and identifying the physiological impact as a function of the medical influence and addiction signature using a physiological machine-learning model, determine an edible as a function of the physiological impact, and generate a nourishment program as a function of the edible.

20 Claims, 7 Drawing Sheets

(51) Int. Cl.
*G06Q 40/02* (2023.01)
*G16H 10/60* (2018.01)
*G16H 40/20* (2018.01)
*G16H 50/20* (2018.01)
*G16H 50/70* (2018.01)
*G16H 70/20* (2018.01)
*G16H 70/60* (2018.01)

(52) U.S. Cl.
CPC ............. *G16H 50/20* (2018.01); *G16H 50/70* (2018.01); *G16H 70/20* (2018.01); *G16H 70/60* (2018.01); *A61B 5/4866* (2013.01)

(58) Field of Classification Search
CPC ...... G16H 70/20; G16H 40/02; A61B 5/4866; A61B 5/00; G06Q 40/02
See application file for complete search history.

(56) References Cited

U.S. PATENT DOCUMENTS

| | | | | |
|---|---|---|---|---|
| 9,710,606 | B2 | 7/2017 | Apte | |
| 9,936,916 | B2 | 4/2018 | Sahin | |
| 10,321,870 | B2* | 6/2019 | Nevo | A61B 5/1112 |
| 10,327,641 | B2 | 6/2019 | Apte | |
| 10,477,342 | B2* | 11/2019 | Williams | A63F 9/12 |
| 10,553,316 | B1* | 2/2020 | Neumann | G06N 20/00 |
| 10,553,319 | B1* | 2/2020 | Neumann | G16H 50/20 |
| 10,559,386 | B1* | 2/2020 | Neumann | G16B 20/00 |
| 2008/0300386 | A1* | 12/2008 | Lazarev | C07K 1/145 |
| | | | | 530/427 |
| 2012/0053070 | A1* | 3/2012 | Blum | C12Q 1/6883 |
| | | | | 506/9 |
| 2016/0012180 | A1* | 1/2016 | Blum | G16B 20/20 |
| | | | | 506/17 |
| 2018/0181701 | A1* | 6/2018 | Niculescu | C12Q 1/6883 |
| 2019/0279281 | A1* | 9/2019 | Kumar | G06Q 30/0631 |
| 2019/0340906 | A1* | 11/2019 | Williams | G08B 21/0277 |
| 2020/0051189 | A1* | 2/2020 | Williams | H04L 67/535 |
| 2020/0289373 | A1* | 9/2020 | Vleugels | A61B 5/1114 |
| 2020/0303074 | A1* | 9/2020 | Mueller-Wolf | A61B 5/7275 |
| 2021/0065909 | A1* | 3/2021 | Donaldson | G16H 10/60 |
| 2021/0084451 | A1* | 3/2021 | Williams | H04W 4/38 |
| 2021/0118559 | A1* | 4/2021 | Lefkofsky | G16B 20/00 |
| 2021/0202067 | A1* | 7/2021 | Williams | A61B 5/0022 |
| 2022/0116736 | A1* | 4/2022 | Williams | G06Q 20/3224 |
| 2022/0277831 | A1* | 9/2022 | Neumann | G16H 50/20 |

OTHER PUBLICATIONS https://link.springer.com/article/10.1007/s10916-018-1071-x; Title: Machine learning for predicting cognitive diseases: methods, data sources and risk factors; By: Brati, Brankica; Date: Oct. 27, 2018.
https://www.mdpi.com/1422-0067/20/11/2842; Title: Frailty, cognitive decline, neurodegenerative diseases and nutrition interventions; By: Gomez-Gomez; Date: 2019/0.6/11.
https://gsconlinepress.com/journals/gscbps/content/functional-foods-and-bioactive-compounds-roles-prevention-treatment-and-management; Title: Roles in the prevention, treatment and management of neurodegenerative diseases; By: Olagunj Abolaji.
https://www.tandfonline.com/doi/abs/10.1080/19390211.2017.1401573; Title: Functional foods and nutraceuticals as dietary intervention in chronic diseases; novel perspectives for health promotion and disease prevention; By: Adefegha, Stephen Adeniyi; Date: Dec. 27, 2017.
https://www.sciencedirect.com/science/article/pii/S0047637413001309; Title: Cognitive decline, dietary factors and gut-brain interactions; By: Caracciolo, Barbara; Date: Dec. 12, 2013.
https://www.ncbi.nlm.nih.gov/pmc/articles/PMC3975244/; Title: Neuroimaging biomarkers of neurodegenerative diseases and dementia; By: Shannon L. Risacher & Andrew J. Saykin; Date: Nov. 14, 2013.
https://www.sciencedirect.com/science/article/pii/S014067361630959X; Title: Diagnosis of multiple sclerosis: progress and challenges; By: Brownlee, Wallace J.; Date: Nov. 24, 2016.
https://www.ncbi.nlm.nih.gov/pmc/articles/PMC6150469/; Title: A novel dynamic hyper-graph inference framework for computer assisted diagnosis of neuro-diseases; By: Zhu, Yingying; Date: May 23, 2017.
https://dl.acm.org/doi/abs/10.1145/3344998; Title: Machine learning techniques for the diagnosis of Alzheimer's disease: A review; By: Tanveer, M.; Date: Apr. 1, 2020.
https://www.hindawi.com/journals/np/2017/3589271/; Title: Lifestyle modulators of neuroplasticity: how physical activity, mental engagement, and diet promote cognitive health during aging; By: Phillips, Christy; Date: Jun. 12, 2017.

* cited by examiner

SYSTEM AND METHOD FOR GENERATING AN ADDICTION NOURISHMENT PROGRAM

FIELD OF THE INVENTION

The present invention generally relates to the field of artificial intelligence. In particular, the present invention is directed to a system and method for generating an addiction nourishment program.

BACKGROUND

Current edible suggestion systems do not account for the status of addictions and/or addiction symptoms. This leads to inefficiency of an edible suggestion system and a poor nutrition plan for the individual. This is further complicated by a lack of uniformity of nutritional plans, which results in dissatisfaction of individuals.

SUMMARY OF THE DISCLOSURE

In an aspect a system for generating an addiction nourishment program includes a computing device, the computing device configured to obtain an addiction element, produce an addiction signature as a function of the addiction element, wherein producing further comprises identifying a predictive signal as a function of an addiction directory, and producing the addiction signature as a function of the predictive signal and addiction element using a predictive machine-learning model, identify a physiological impact as a function of the addiction signature, wherein identifying a physiological impact further comprises receiving a medical influence and identifying the physiological impact as a function of the medical influence and addiction signature using a physiological machine-learning model, determine an edible as a function of the physiological impact, and generate a nourishment program as a function of the edible.

In another aspect a method for generating an addiction nourishment program includes obtaining, by a computing device, an addiction element, producing, by the computing device, an addiction signature as a function of the addiction element, wherein producing further comprises identifying a predictive signal as a function of an addiction directory, and producing the addiction signature as a function of the predictive signal and addiction element using a predictive machine-learning model, identifying, by the computing device, a physiological impact as a function of the addiction signature, wherein identifying a physiological impact further comprises receiving a medical influence and identifying the physiological impact as a function of the medical influence and addiction signature using a physiological machine-learning model, determining, by the computing device, an edible as a function of the physiological impact, and generating, by the computing device, a nourishment program as a function of the edible.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating an addiction nourishment program. In an embodiment, this disclosure may obtain an addiction element that relates to an individual. Aspects of the present disclosure may be used to produce an addiction signature that may identify one or more addiction of an individual. This is so, at least in part, because this disclosure incorporates a machine-learning model. Aspects of the present disclosure can also be used to identify a physiological impact as a function of the addiction signature. Aspects of the present disclosure can be used to determine an edible as a function of the physiological impact on the individual. Aspects of the present disclosure allow for generating a nourishment program as a function of the determined edible for the physiological impact. Exemplary embodiments illustrating aspects of the present disclosure are described below in the context of several specific examples.

Figure 1:
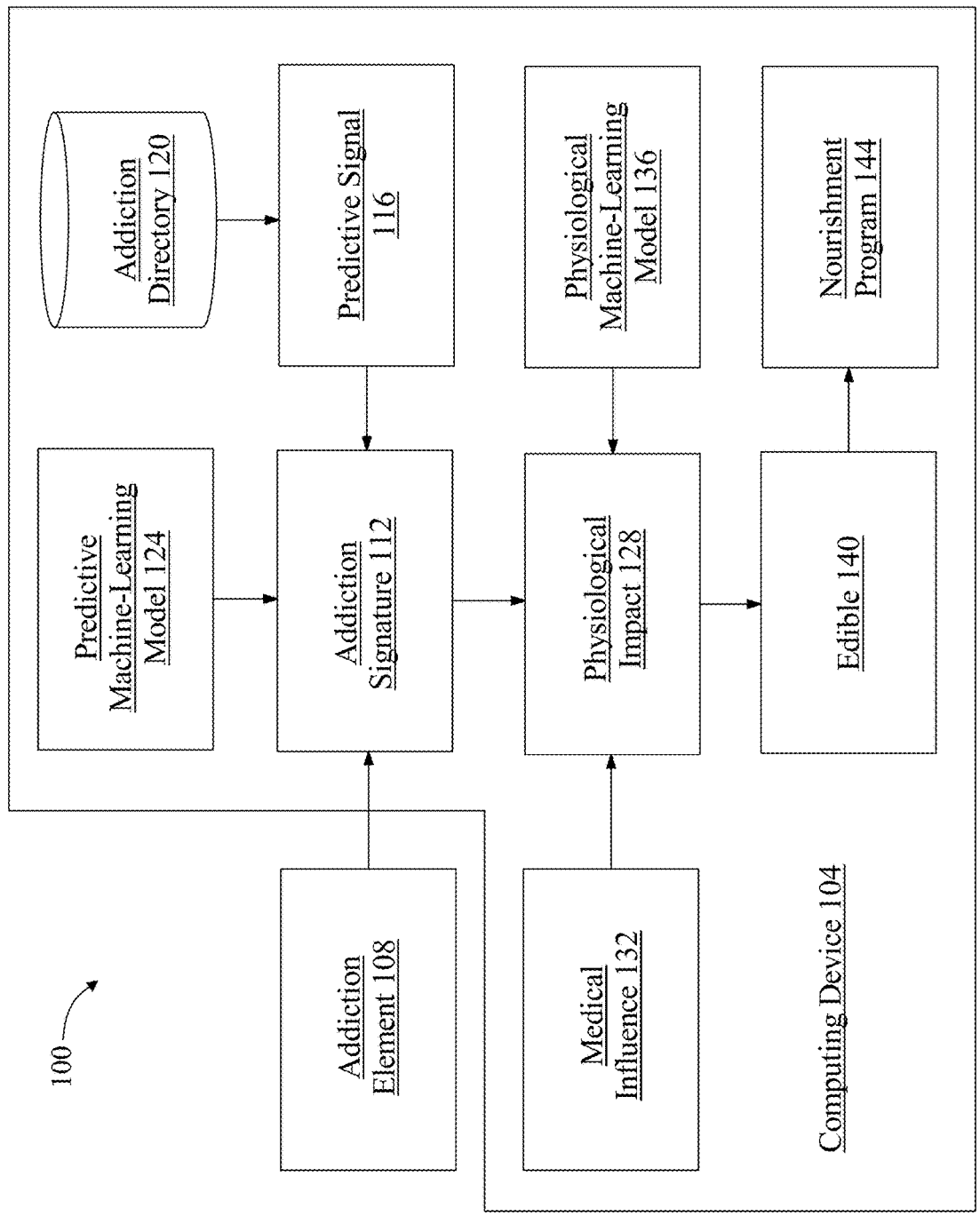
FIG. 1 is a block diagram illustrating an exemplary embodiment of a system for generating an addiction nourishment program.

Referring now to FIG. 1, an exemplary embodiment of a system 100 for generating an addiction nourishment program is illustrated. System includes a computing device 104. computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 obtains an addiction element 108. As used in this disclosure an "addiction element" is an element of data associated with an addiction. In an embodiment addiction element 108 may include an element that denotes an individual's system health status in relation to an addiction, wherein a system health status is a biological evaluation of an individual's body. Addiction element 108 may include a biological sample. As used in this disclosure a "biological sample" is one or more biological specimens collected from an individual. Biological sample may include, without limitation, exhalate, blood, sputum, urine, saliva, feces, semen, and other bodily fluids, as well as tissue. Addiction element 108 may include a biological sampling device. Addiction element 108 may include one or more biomarkers. As used in this disclosure a "biomarker" is a molecule and/or chemical that identifies the health status of a user's health system. As a non-limiting example, biomarkers may include, alpha-tubulin, 4-HNE, Collagen type I, Collagen type II, ALDH2, AMPK, Calmodulin, Cytochrome C oxidase, CYP2E1, electron transfer flavoprotein, ERK1, ERK2, Glutathione S-transferase, GRP78, Ketosteroid reductase, Surfactant Protein D, Albumin, Carbonic Anhydrase, Hemoglobin, Acetaldehyde, VLDL, LDL, Coagulation factors, and the like thereof. As a further non-limiting example, addiction element 108 may include datum from one or more devices that collect, store, and/or calculate one or more lights, voltages, currents, sounds, chemicals, pressures, and the like thereof that are associated with the user's health system.

In an embodiment, and without limitation, addiction element 108 may include one or more elements of a negative behavior. As used in this disclosure a "negative behavior" is a self-injurious behavior that may be objectively monitored and/or characterized. For example, and without limitation, negative behavior may include, without limitation, use of an illicit chemical substance, such as narcotics, stimulants such as cocaine, cocaine derivatives, amphetamines, methamphetamine, nicotine, or the like, opiates such as heroine, fentanyl, oxycodone, or the like, cannabis, cannabis-derived compounds such as THC, depressants such as alcohol, barbiturates, benzodiazepines, or the like, MDMA, PCP, hallucinogens such as LSD, addictions to any of various prescription drugs, or the like. As a further non-limiting example, negative behavior may include a compulsive act, such as a compulsive gambling, compulsive engagement in sexual activity, compulsive sexual activity concurrent with pornography consumption, compulsive use of Internet or video games, compulsive or continuous gambling despite resulting financial harm, food addiction as characterized by compulsive overeating, an eating disorder such as anorexia or bulimia, or the like. Negative behavior may additionally or alternatively include any negative behavior used as a negative behavior, and/or any method for detection and/or identification thereof, as described in U.S. Nonprovisional application Ser. No. 16/673,673 filed on Nov. 4, 2019 and entitled "SYSTEMS AND METHODS FOR CLASSIFYING MEDIA ACCORDING TO USER NEGATIVE PROPENSITIES," the entirety of which is incorporated herein by reference.

As an illustrative example, biological extraction may include a genetic sequence; a "genetic sequence," as used herein, is a series of genes identified in a nucleotide sequence of chromosomal nucleic acid of a human subject, including without limitation deoxyribonucleic acid (DNA) and/or ribonucleic acid (RNA). DNA may include chromosomal DNA, including without limitation sequences encoding particular genes as well as sequences of DNA disposed between or after gene sequences. A genetic sample may include mRNA, tRNA, or any other RNA sequence or strand. Genetic sequence may be a complete sequence of genes of the subject and/or a subset thereof.

Genetic data may be extracted from a human subject by means of a physically extracted sample. Physically extracted sample may include without limitation a tissue sample, a buccal swab, a fluid sample, a biopsy or the like. Extraction of genetic samples may be performed using any suitable physical process, including separation of nucleic acid from other tissue and/or fluid elements using, without limitation, a centrifuge. Extraction may include any form of restriction or division of a DNA and/or RNA sequence into subsequences, including without limitation using restriction enzymes. Extraction of genetic samples may include one or more variations of polymerase chain reaction "PCR" processes, whereby a particular strand of nucleic acid is replicated or "amplified" in a solution of nucleic acid by repeatedly exposing the solution to stimulus, such as heat, that breaks base-pair bonds, and then removing the stimulus to allow base-pair bonds to reform; as a result, a strand or sequence of nucleic acid will bond to free-floating molecules of nucleic acid, forming an inverse copy of itself, which will be separated from the strand or sequence during stimulus, and subsequently each of the strand and the inverse copy will bond to further free-floating molecules. As the above-described process is repeated, the number of copies of the strand or sequence increases exponentially. Extraction may include any suitable process to measure sequence lengths, match sequences, or the like, including without limitation electrophoresis.

Received biological extraction, including without limitation any received genetic sequence, may be stored in any suitable manner, including without limitation in a user database. User database may include any data structure suitable for use as vice database as described above. Data entries in a user database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database may reflect categories of data consistently with this disclosure.

Computing device 104 is configured to identify, using the biological extraction and the behavior model, a negative behavioral propensity associated with the human subject. For instance, and without limitation, computing device 104 may generate a plurality of gene combinations from genetic sequence and input such gene combinations to genetic behavior model; genetic behavior model may identify one or more negative behavioral propensities and/or negative behaviors, which may be referred to interchangeably herein as "problematic behaviors" to which one or more gene combinations from genetic sequence are classified.

An exemplary embodiment of a method of classifying media according to user negative propensities is illustrated. Computing device 104 identifies a negative behavioral propensity associated with a human subject. This may be implemented, without limitation, as described above. For instance, computing device may identify negative behavioral propensity by generating, using a first feature learning algorithm, in training data containing a plurality of pairs of genetic sequences and negative behavioral propensities, a genetic behavior model correlating gene combinations with negative behavioral propensities, receiving a genetic sequence, the genetic sequence including a series of genes identified in a nucleotide sequence of chromosomal nucleic acid of a human subject, and identifying using the genetic sequence and the genetic behavior model, a negative behavioral propensity associated with the human subject; this may be performed, without limitation as described above. First feature learning algorithm may include a k-means clustering algorithm.

Still referring to FIG. 1, computing device 104 may obtain addiction element 108 by receiving an input from a user. As used in this disclosure "input" is an element of datum that is obtained by the user. In an embodiment, and without limitation, input may include one or more inputs from a family member. For example, and without limitation, a brother, sister, mother, father, cousin, aunt, uncle, grandparent, child, friend, and the like thereof may enter to computing device 104 that an individual may be suffering from an addiction. Input may include one or more inputs from an informed advisor as a function of a medical assessment, wherein a "medical assessment" is an evaluation and/or estimation of the health status of the health system of the individual. As used in this disclosure "informed advisor" is an individual that is skilled in a particular area relating to the study of the health system of the individual. As a non-limiting example an informed advisor may include a medical professional who may assist and/or participate in the medical treatment of an individual's health system including, but not limited to, psychiatrists, psychologists, family physicians, pain management physicians, pediatricians, addiction medicine physicians, substance abuse physicians, osteopathic physicians, and the like thereof. As a non-limiting example input may include an informed advisor that enters a medical assessment comprising a blood analysis, urine analysis, stool analysis, saliva analysis, skin analysis, and the like thereof. Additionally or alternatively, input may include one or more medical records and/or patient charts that identify an individual's previous experience with a substance.

In an embodiment, and without limitation, input may include one or more financial histories of an individual. As used in this disclosure a "financial history" is a history of transactions made by an individual. For example, and without limitation, financial history may include identifying a bank statement that includes $2,000.00 a week on alcohol. As a further non-limiting example, financial history may include identifying a bank statement that includes transactions to a known illicit drug supplier. Additionally or alternatively, input may include a social media history. As used in this disclosure a "social media history" is a history of social media interactions made by an individual. For example, and without limitation, social media history may determine that a user is interacting with social media for more than 20 hours in a day. As a further non-limiting example, social media history may determine one or more previous social media posts and/or social media interactions that may relate to an addiction.

Still referring to FIG. 1, computing device 104 produces an addiction signature 112 as a function of addiction element 108. As used in this disclosure an "addiction signature" is a profile of an individual that relates to a tendency for an addictive habit. For example, and without limitation, addiction signature 112 may denote that an individual has addiction elements that may relate to one or more alcoholism addictions. Computing device 104 produces addiction signature 112 as a function of identifying a predictive signal 116. As used in this disclosure a "predictive signal" is a signal that represents the likelihood of a user developing an addiction. As a non-limiting example, predictive signal 116 may identify a high likelihood that a user is developing an addiction of social media as a function of enhanced social media interactions. As a further non-limiting example, predictive signal 116 may identify a low likelihood that a user is developing an opioid addiction as a function of ending a medical treatment and refraining from requesting a refill. As a further non-limiting example, predictive signal 116 may identify a user has a high likelihood for developing a gambling addiction as a function of frequent visits to pawn shops and casinos. Predictive signal 116 is identified as a function of an addiction directory 120. As used in this disclosure an "addiction directory" is a database that collects, stores, and/or transmits data associated with addictions. For example, addiction directory 120 may collect, store, and/or transmit data associated with an internet addiction. As a further non-limiting example, addiction directory 120 may collect, store, and/or transmit data associated with a narcotic addiction.

In an embodiment, and without limitation, computing device 104 may produce addiction signature 112 as a function of determining a rehabilitation phase. As used in this disclosure a "rehabilitation phase" is phase that an individual is progressing through in a rehabilitation process, as described in further detail below, in reference to FIG. 2. For example, and without limitation, rehabilitation phase may include one or more denial phases, loss of control phases, deterioration phases, detoxification phases, treatment phases, long-term phases, and the like thereof. Additionally or alternatively, computing device 104 may produce addiction signature 112 as a function of determining an addiction dysfunction. As used in this disclosure an "addiction dysfunction" is an addiction that is a disease and/or disorder. For example, and without limitation, an addiction dysfunction may include alcoholism, marijuana addictions, amphetamine addictions, cocaine addictions, nicotine addictions, opioid addictions, food addictions, chocolate addictions, video game addictions, gambling addictions, sexual addictions, social media addictions, and the like thereof.

Still referring to FIG. 1, computing device 104 produces addiction signature 112 as a function of predictive signal 116 and addiction element 108 using a predictive machine-learning model 124. As used in this disclosure "predictive machine-learning model" is a machine-learning model to produce an addiction signature output given predictive signals and addiction elements as inputs; this is in contrast to a non-machine learning software program where the commands to be executed are determined in advance by a user and written in a programming language. Predictive machine-learning model 124 may include one or more predictive machine-learning processes such as supervised, unsupervised, or reinforcement machine-learning processes that computing device 104 and/or a remote device may or may not use in the determination of addiction signature 112. As used in this disclosure "remote device" is an external device to computing device 104. A predictive machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train predictive machine-learning process as a function of a predictive training set. As used in this disclosure "predictive training set" is a training set that correlates a predictive signal and/or addiction element to an addiction signature. For example, and without limitation, a predictive signal of a high likelihood for developing alcoholism and an addiction element enhanced CYP450 enzymes may relate to an addiction signature of an addictive habit of consuming alcohol. The predictive training set may be received as a function of user-entered valuations of predictive signals, addiction elements, and/or addiction signatures. Computing device 104 may receive predictive training set by receiving correlations of predictive signals, and/or addiction elements that were previously received and/or determined during a previous iteration of determining addiction signatures. The predictive training set may be received by one or more remote devices that at least correlate a predictive signal and/or addiction element to an addiction signature. As used in this disclosure "remote device" is an external device to computing device 104. The predictive training set may be received in the form of one or more user-entered correlations of a predictive signal and/or addiction element to an addiction signature. Additionally or alternatively, a user may include an informed advisor, wherein an informed advisor may include, without limitation, psychiatrists, psychologists, family physicians, pain management physicians, pediatricians, addiction medicine physicians, substance abuse physicians, osteopathic physicians, and the like thereof.

Still referring to FIG. 1, computing device 104 may receive predictive machine-learning model from a remote device that utilizes one or more predictive machine learning processes, wherein a remote device is described above in detail. For example, and without limitation, a remote device may include a computing device, external device, processor, and the like thereof. Remote device may perform the predictive machine-learning process using the predictive training set to generate addiction signature 112 and transmit the output to computing device 104. Remote device may transmit a signal, bit, datum, or parameter to computing device 104 that at least relates to addiction signature 112. Additionally or alternatively, the remote device may provide an updated machine-learning model. For example, and without limitation, an updated machine-learning model may be comprised of a firmware update, a software update, a predictive machine-learning process correction, and the like thereof. As a non-limiting example a software update may incorporate a new predictive signal that relates to a modified addiction element. Additionally or alternatively, the updated machine learning model may be transmitted to the remote device, wherein the remote device may replace the predictive machine-learning model with the updated machine-learning model and determine the addiction signature as a function of the predictive signal using the updated machine-learning model. The updated machine-learning model may be transmitted by the remote device and received by computing device 104 as a software update, firmware update, or corrected predictive machine-learning model. For example, and without limitation predictive machine-learning model may utilize a random forest machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device may produce addiction signature 112 as a function of a classifier. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device identifies a physiological impact 128 as a function of addiction signature 112. As used in this disclosure a "physiological impact" is an effect that an addiction has on the health system of an individual. For example, and without limitation, physiological impact 128 may include one or more psychological symptoms including, but not limited to, an inability to stop using, use and abuse of substances despite health problems, obsession, risky behavior, and the like thereof. As a further non-limiting example, physiological impact 128 may include one or more social symptoms. As used in this disclosure a "social symptom" is a symptom of an addiction that impacts the way an individual socializes with and/or relates to other individuals. Social symptom may include, but it's not limited to sacrifices, dropping hobbies and activities, maintaining a good supply of substances, secrecy, solitude, denial, legal issues, financial difficulties, and the like thereof. As a non-limiting example, social symptom may include an individual that stops partaking in pastimes they enjoy in order to add more time for their addiction. As a further non-limiting example, social symptom may include an individual that denies the use of a substance and/or denies an addiction. As a further non-limiting example, social symptom may include an individual that exhibits secrecy and/or solitude from previous friends, family, and/or colleagues. As a further non-limiting example, physiological impact 128 may include one or more physical symptoms including, but not limited to, cravings, constipation, diarrhea, trembling, seizures, sweats, changes in appetite, limb damage, respiratory distress, sleeplessness, and the like thereof. Computing device identifies physiological impact 128 as a function of receiving a medical influence 132. As used in this disclosure a "medical influence" is an influence that addiction element 108 has on the body. For example, and without limitation medical influence 132 may include one or more influences such as gene expression, sensitization, neuroepigenetic mechanisms, and the like thereof, as described in detail below, in reference to FIG. 4. In an embodiment, and without limitation, medical influence 132 may include one or more reward system changes, wherein the reward system may include the mesolimbic pathway, the mesocorticolimbic pathway, and the like thereof. In a non-limiting example, medical influence 132 may be received as a function of obtaining one or more medical sources, such as medical textbooks, medical societies, medical organizations, medical websites, and the like thereof. For example, and without limitation, medical influence 132 may be received as a function of a medical textbook such as The Clinical Textbook of Addictive Disorders. As a further non-limiting example, medical influence 132 may be received as a function of a medical website such as WebMD.com, and/or MayoClinic.org.

Physiological impact 128 is identified as a function of medical influence 132 and addiction signature 112 using a physiological machine-learning model 136. As used in this disclosure a "physiological machine-learning model" is a machine-learning model to produce a physiological impact output given medical influences and addiction signatures as inputs; this is in contrast to a non-machine learning software program where the commands to be executed are determined in advance by a user and written in a programming language. Physiological machine-learning model may include one or more physiological machine-learning processes such as supervised, unsupervised, or reinforcement machine-learning processes that computing device 104 and/or a remote device may or may not use in the determination of physiological impact 128, wherein a remote device is an external device to computing device 104 as described above in detail. A physiological machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train physiological machine-learning process as a function of a physiological training set. As used in this disclosure a "physiological training set" is a training set that correlates at least medical influence and addiction signature to a physiological impact. For example, and without limitation, medical influence of deltaFosB expression and an addiction signature of a methamphetamine addiction may relate to a physiological impact of reduced thickness of the Blood brain barrier. The physiological training set may be received as a function of user-entered valuations of medical influences, addiction signatures, and/or physiological impacts. Computing device 104 may receive physiological training set by receiving correlations of medical influences and/or addiction signatures that were previously received and/or determined during a previous iteration of determining physiological impacts. The physiological training set may be received by one or more remote devices that at least correlate a medical influence and addiction signature to a physiological impact, wherein a remote device is an external device to computing device 104, as described above. Physiological training set may be received in the form of one or more user-entered correlations of a medical influence and/or addiction signature to a physiological impact. Additionally or alternatively, a user may include an informed advisor, wherein an informed advisor may include, without limitation, psychiatrists, psychologists, family physicians, pain management physicians, pediatricians, addiction medicine physicians, substance abuse physicians, osteopathic physicians, and the like thereof.

Still referring to FIG. 1, computing device 104 may receive physiological machine-learning model 136 from a remote device that utilizes one or more physiological machine learning processes, wherein remote device is described above in detail. For example, and without limitation, remote device may include a computing device, external device, processor, and the like thereof. Remote device may perform the physiological machine-learning process using the physiological training set to generate physiological impact 128 and transmit the output to computing device 104. Remote device may transmit a signal, bit, datum, or parameter to computing device 104 that at least relates to physiological impact 128. Additionally or alternatively, the remote device may provide an updated machine-learning model. For example, and without limitation, an updated machine-learning model may be comprised of a firmware update, a software update, a physiological machine-learning process correction, and the like thereof. As a non-limiting example a software update may incorporate a new medical influence that relates to a modified addiction signature. Additionally or alternatively, the updated machine learning model may be transmitted to the remote device, wherein the remote device may replace the physiological machine-learning model with the updated machine-learning model and determine the physiological as a function of the addiction signature using the updated machine-learning model. The updated machine-learning model may be transmitted by the remote device and received by computing device 104 as a software update, firmware update, or corrected physiological machine-learning model. For example, and without limitation a physiological machine-learning model 136 may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference. In an embodiment, and without limitation, physiological machine-learning model 136 may identify physiological impact 128 as a function of one or more classifiers, wherein a classifier is described above in detail.

Still referring to FIG. 1, computing device 104 determines an edible 140 as a function of physiological impact 128. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. Computing device 104 may determine edible 140 as a function of receiving a nourishment composition. As used in this disclosure a "nourishment composition" is a list and/or compilation of all of the nutrients contained in an edible. As a non-limiting example nourishment composition may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition may be obtained as a function of an edible directory, wherein an "edible directory" is a database of edibles that may be identified as a function of one or more metabolic components, as described in detail below, in reference to FIG. 3.

Still referring to FIG. 1, computing device 104 may determine edible 140 as a function of a withdrawal element. As used in this disclosure a "withdrawal element" is an element that relates to an individual exhibiting withdrawal symptoms. For example, and without limitation, withdrawal element may include one or more elements of anxiety, sweating, vomiting, diarrhea, irritability, fatigue, shaking, sweating, nausea, headache, and the like thereof. In an embodiment and without limitation, computing device 104 may determine a withdrawal element and determine edible 140 as a function of reducing the likelihood for withdrawal element to form. For example, and without limitation, a withdrawal element of shaking for the addiction of alcohol may be determined, wherein an edible of legumes and/or fruits may be determined to aid in reducing tremors and/or shaking of the peripheral nervous system.

Still referring to FIG. 1, computing device 104 may produce a nourishment demand as a function of physiological impact 128. As used in this disclosure a "nourishment demand" is requirement and/or necessary amount of nutrients required for a user to consume. As a non-limiting example, nourishment demand may include a user requirement of 32 g of omega-3-fatty acid to be consumed per day. Nourishment demand may be determined as a function of receiving a nourishment goal. As used in this disclosure a "nourishment goal" is a recommended amount of nutrients that a user should consume. Nourishment goal may be identified by one or more organizations that relate to, represent, and/or study addictions in humans, such as the American Medical Association, American Society of Addiction Medicine, Addiction Free Forever, Alcoholics Anonymous, Cenikor Foundation, Greenway Recovery Center, Hope Heaven, and the like thereof.

Still referring to FIG. 1, computing device 104 identifies edible 140 as a function of nourishment composition, nourishment demand, and an edible machine-learning model. As used in this disclosure a "edible machine-learning model" is a machine-learning model to produce an edible output given nourishment compositions and nourishment demands as inputs; this is in contrast to a non-machine learning software program where the commands to be executed are determined in advance by a user and written in a programming language. Edible machine-learning model may include one or more edible machine-learning processes such as supervised, unsupervised, or reinforcement machine-learning processes that computing device 104 and/or a remote device may or may not use in the determination of edible 140, wherein a remote device is an external device to computing device 104 as described above in detail. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure an "edible training set" is a training set that correlates at least nourishment composition and nourishment demand to an edible. For example, and without limitation, nourishment composition of 12 mg of tryptophan and a nourishment demand of 8 g of tryptophan as a function of a cocaine addiction may relate to an edible of bananas. The edible training set may be received as a function of user-entered valuations of nourishment compositions, nourishment demands, and/or edibles. Computing device 104 may receive edible training set by receiving correlations of nourishment compositions and/or nourishment demands that were previously received and/or determined during a previous iteration of determining edibles. The edible training set may be received by one or more remote devices that at least correlate a nourishment composition and nourishment demand to an edible, wherein a remote device is an external device to computing device 104, as described above. Edible training set may be received in the form of one or more user-entered correlations of a nourishment composition and/or nourishment demand to an edible. Additionally or alternatively, a user may include an informed advisor, wherein an informed advisor may include, without limitation, psychiatrists, psychologists, family physicians, pain management physicians, pediatricians, addiction medicine physicians, substance abuse physicians, osteopathic physicians, and the like thereof.

Still referring to FIG. 1, computing device 104 may receive edible machine-learning model from a remote device that utilizes one or more edible machine learning processes, wherein remote device is described above in detail. For example, and without limitation, remote device may include a computing device, external device, processor, and the like thereof. Remote device may perform the edible machine-learning process using the edible training set to generate edible 140 and transmit the output to computing device 104. Remote device may transmit a signal, bit, datum, or parameter to computing device 104 that at least relates to edible 140. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified nourishment demand. Additionally or alternatively, the updated machine learning model may be transmitted to the remote device, wherein the remote device may replace the edible machine-learning model with the updated machine-learning model and determine the edible as a function of the nourishment demand using the updated machine-learning model. The updated machine-learning model may be transmitted by the remote device and received by computing device 104 as a software update, firmware update, or corrected edible machine-learning model. For example, and without limitation an edible machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference. In an embodiment, and without limitation, edible machine-learning model may identify edible 140 as a function of one or more classifiers, wherein a classifier is described above in detail.

Still referring to FIG. 1, computing device 104 may identify edible as a function of a likelihood parameter. As used in this disclosure a "likelihood parameter" is a parameter that identities the probability of a user to consume an edible. As a non-limiting example likelihood parameter may identify a high probability that a user will consume an edible of chicken. As a further non-limiting example likelihood parameter may identify a low probability that a user will consume an edible of anchovies. Likelihood parameter may be determined as a function of a user taste profile. As used in this disclosure a "user taste profile" is a profile of a user that identifies one or more desires, preferences, wishes, and/or wants that a user has. As a non-limiting example a user taste profile may include a user's preference for chicken flavor and/or crunchy textured edibles. Likelihood parameter may be determined as a function of an edible profile. As used in this disclosure an "edible profile" is taste of an edible is the sensation of flavor perceived in the mouth and throat on contact with the edible. Edible profile may include one or more flavor variables. As used in this disclosure a "flavor variable" is a variable associated with the distinctive taste of an edible, wherein a distinctive may include, without limitation sweet, bitter, sour, salty, umami, cool, and/or hot. Edible profile may be determined as a function of receiving flavor variable from a flavor directory. As used in this disclosure a "flavor directory" is a database or other data structure including flavors for an edible. As a non-limiting example flavor directory may include a list and/or collection of edibles that all contain umami flavor variables. As a further non-limiting example flavor directory may include a list and/or collection of edibles that all contain sour flavor variables. Flavor directory may be implemented similarly to an edible directory as described below in detail, in reference to FIG. 3. Likelihood parameter may alternatively or additionally include any user taste profile and/or edible profile used as a likelihood parameter as described in U.S. Nonprovisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, computing device 104 generates a nourishment program 144 as a function of edible 140. As used in this disclosure a "nourishment program" is a program consisting of one or more edibles that are to be consumed over a given time period, wherein a time period is a temporal measurement such as seconds, minutes, hours, days, weeks, months, years, and the like thereof. As a non-limiting example nourishment program 144 may consist of recommending oysters for 8 days. As a further non-limiting example nourishment program 144 may recommend tofu for a first day, milk and cookies for a second day, and artichokes for a third day. Nourishment program 144 may include one or more diet programs such as paleo, keto, vegan, vegetarian, and the like thereof. Computing device 104 may develop nourishment program 144 as a function of an addiction outcome. As used in this disclosure an "addiction outcome" is an outcome that an edible may generate according to a predicted and/or purposeful plan. As a non-limiting example, addiction outcome may include a treatment outcome. As used in this disclosure a "treatment outcome" is an intended outcome that is designed to at least reverse and/or eliminate physical impact 128, addiction signature 112, addiction element 108 and/or addiction dysfunction. As a non-limiting example, a treatment outcome may include reversing the effects of the addiction dysfunction associated with social media. As a further non-limiting example, a treatment outcome includes reversing the addiction dysfunction of associated with cannabis. Addiction outcome may include a prevention outcome. As used in this disclosure a "prevention outcome" is an intended outcome that is designed to at least prevent and/or avert physical impact 128, addiction signature 112, addiction element 108 and/or addiction dysfunction. As a non-limiting example, a prevention outcome may include preventing the development of the addiction dysfunction associated with cocaine.

In an embodiment, and still referring to FIG. 1, addiction dysfunction may include one or more addictions associated with a user behavior modification. As used in this disclosure a "user behavior modification" is a modification to an addiction that a user desires to alter. For example, and without limitation, a behavior modification may include physical addictions to substances such as alcohol, tobacco, opioids, prescription drugs, cocaine, cannabis, amphetamines, hallucinogens, inhalants, phencyclidine and the like. User behavior modification may include impulse control disorders such as intermittent explosive disorder, kleptomania, pyromania, gambling and the like. User behavior modification may include addictions to certain actions such as food, sex, pornography, computer use, device use such as cellphones, tablets, and the like; work, exercise, spiritual obsession, pain seeking, cutting, shopping and the like. User behavior modification may include modification to a trait one may exhibit in personal relationships at home, work, or school such as winning too much, passing judgment, making destructive comments, speaking when angry, extreme negativity, withholding information, making excuses, clinging to the past, playing favorites, failing to listen, failing to express gratitude, and the like. User behavior modification may include modification to thoughts, words, actions and deeds such as sexual immorality including impurity, orgies, and lust, idolatry including witchcraft, selfish ambition, demons, and demigods, debauchery including drunkenness, filthy language, and corruption, hatred including malice, deceit, and fits of rage, jealousy including envy, anger, greed and slander. User behavior modification may include modification to a trait a user may exhibit surrounding one's lifestyle such as a desire to lose weight, attend training sessions at a gym more frequently, develop a meditation practice, meet with a nutrition professional to discuss meal plans and the like. User behavior modification may include modification to a trait a user seeks to attain. User behavior modification may additionally or alternatively include any behavior modification used as a behavior modification as described in U.S. Nonprovisional application Ser. No. 16/825,359 filed on Mar. 20, 2020 and entitled "METHODS AND SYSTEMS FOR AN ARTIFICIAL INTELLIGENCE SUPPORT NETWORK FOR VIBRANT CONSTITUTIONAL GUIDANCE," the entirety of which is incorporated herein by reference.

Still referring to FIG. 1, computing device 104 may develop nourishment program 144 as a function of edible 140 and addiction outcome using a nourishment machine-learning model. As used in this disclosure a "nourishment machine-learning model" is a machine-learning model to produce a nourishment program output given edibles and/or addiction outcomes as inputs; this is in contrast to a non-machine learning software program where the commands to be executed are determined in advance by a user and written in a programming language. Nourishment machine-learning model may include one or more nourishment machine-learning processes such as supervised, unsupervised, or reinforcement machine-learning processes that computing device 104 and/or a remote device may or may not use in the development of nourishment program 144. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates an addiction outcome to an edible. The nourishment training set may be received as a function of user-entered edibles, addiction outcomes, and/or nourishment programs. For example, and without limitation, an addiction outcome of treating alcoholism may correlate to an edible of turkey breast and/or tuna. Computing device 104 may receive nourishment training by receiving correlations of addiction outcomes and/or edibles that were previously received and/or determined during a previous iteration of developing nourishment programs. The nourishment training set may be received by one or more remote devices that at least correlate an addiction outcome and/or edible to a nourishment program, wherein a remote device is an external device to computing device 104, as described above. Nourishment training set may be received in the form of one or more user-entered correlations of an addiction outcome and/or edible to a nourishment program. Additionally or alternatively, a user may include an informed advisor, wherein an informed advisor may include, without limitation, psychiatrists, psychologists, family physicians, pain management physicians, pediatricians, addiction medicine physicians, substance abuse physicians, osteopathic physicians, and the like thereof.

Still referring to FIG. 1, computing device 104 may receive nourishment machine-learning model from the remote device that utilizes one or more nourishment machine learning processes, wherein a remote device is described above in detail. For example, and without limitation, a remote device may include a computing device, external device, processor, and the like thereof. The remote device may perform the nourishment machine-learning process using the nourishment training set to develop nourishment program 144 and transmit the output to computing device 104. The remote device may transmit a signal, bit, datum, or parameter to computing device 104 that at least relates to nourishment program 144. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new addiction outcome that relates to a modified edible. Additionally or alternatively, the updated machine learning model may be transmitted to the remote device, wherein the remote device may replace the nourishment machine-learning model with the updated machine-learning model and develop the nourishment program as a function of the addiction outcome using the updated machine-learning model. The updated machine-learning model may be transmitted by the remote device and received by computing device 104 as a software update, firmware update, or corrected nourishment machine-learning model. For example, and without limitation nourishment machine-learning model may utilize a neural net machine-learning process, wherein the updated machine-learning model may incorporate decision tree machine-learning processes.

Figure 2:
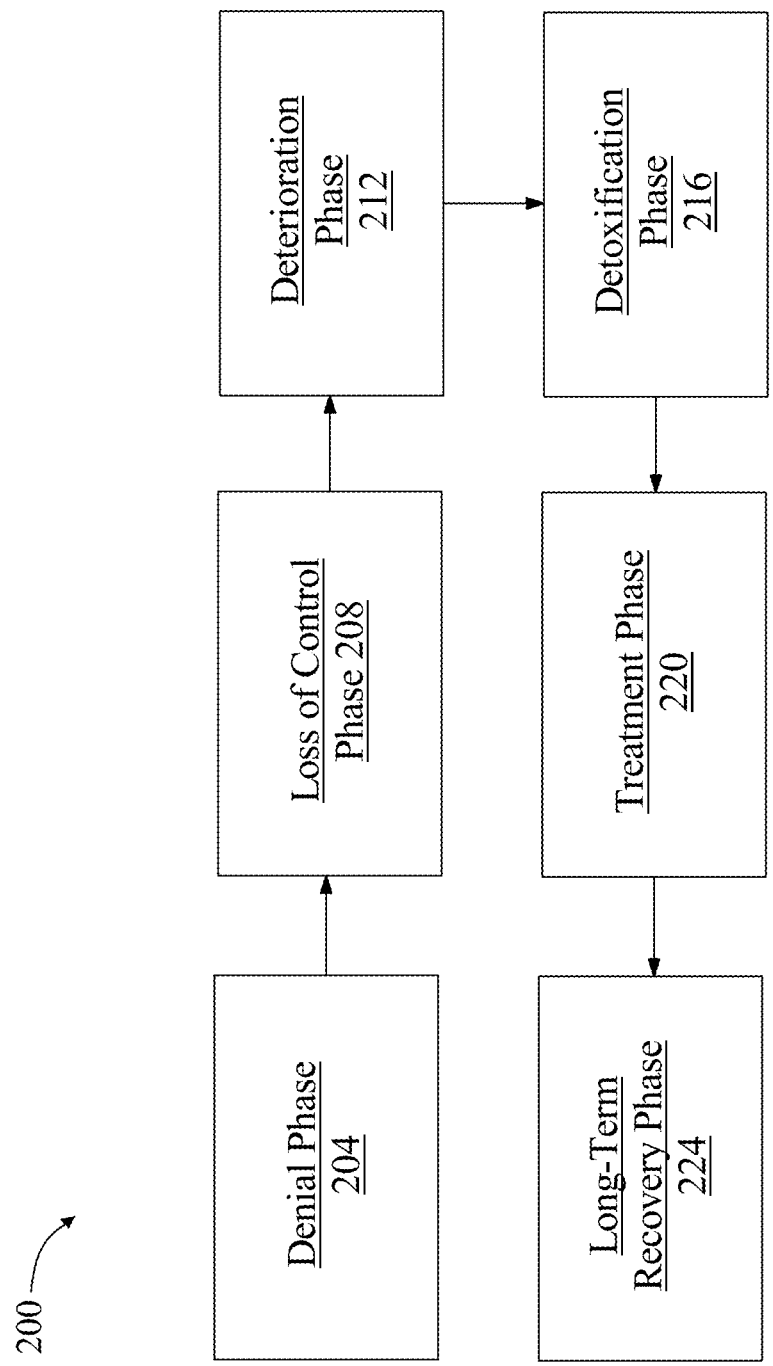
FIG. 2 is a block diagram of an exemplary embodiment of a rehabilitation phase according to an embodiment of the invention.

Now referring to FIG. 2, an exemplary embodiment 200 of a rehabilitation phase is illustrated. Rehabilitation phase may include a denial phase 204. As used in this disclosure a "denial phase" is a phase wherein the individual denies and/or lies about the use of the substance. For example, and without limitation, denial phase 204 may include one or more behaviors associated with blame, concealing, defensiveness, dismissing, false agreement, making comparisons, rationalization, and the like thereof. Rehabilitation phase may include a loss of control phase 208. As used in this disclosure a "loss of control phase" is a phase wherein the individual begins and/or continues to abuse the substance. For example, and without limitation, loss of control phase 208 may include one or more behaviors associated with a desire to abuse the substance more frequently, blackouts as a function of the substance, withdrawal symptoms begin to develop if no substance is used, substance habits begin to form, and the like thereof. Rehabilitation phase may include a loss of deterioration phase 212. As used in this disclosure a "deterioration phase" is a phase wherein the individual experiences severe physical and emotional consequences as a result of an addiction. For example, and without limitation, deterioration phase 212 may include one or more behaviors associated with an obsession of the substance, substance required functioning, loss of interests outside of that substance, depression, anxiety, insomnia, financial hardship, legal issues, relationship hardships, serious health problems, and the like thereof. Rehabilitation phase may include a loss of detoxification phase 216. As used in this disclosure a "detoxification phase" is a phase wherein the individual abstains from consuming, smoking, and/or injecting the substance. For example, and without limitation, detoxification phase 216 may include one or more behaviors associated with remaining sober from alcohol, no longer injecting heroin, avoiding cell phone usage, and the like thereof. Rehabilitation phase may include a loss of treatment phase 220. As used in this disclosure a "treatment phase" is a phase wherein the individual seeks treatment and/or enters a treatment program for the addiction. For example, and without limitation, treatment phase 220 may include an individual that is receiving medical care such as nicotine patches to aid in treating the addiction and reduce the effects of the addiction. Rehabilitation phase may include a loss of long-term recovery phase 224. As used in this disclosure a "long-term recovery phase" is a phase wherein the individual is treated to address long-term dysfunctions as a result of the addiction. For example, and without limitation, long-term recovery phase 224 may include an individual that seeks to treatment to repair and/or correct behavior problems, emotional issues, and/or psychological trauma.

Figure 3:
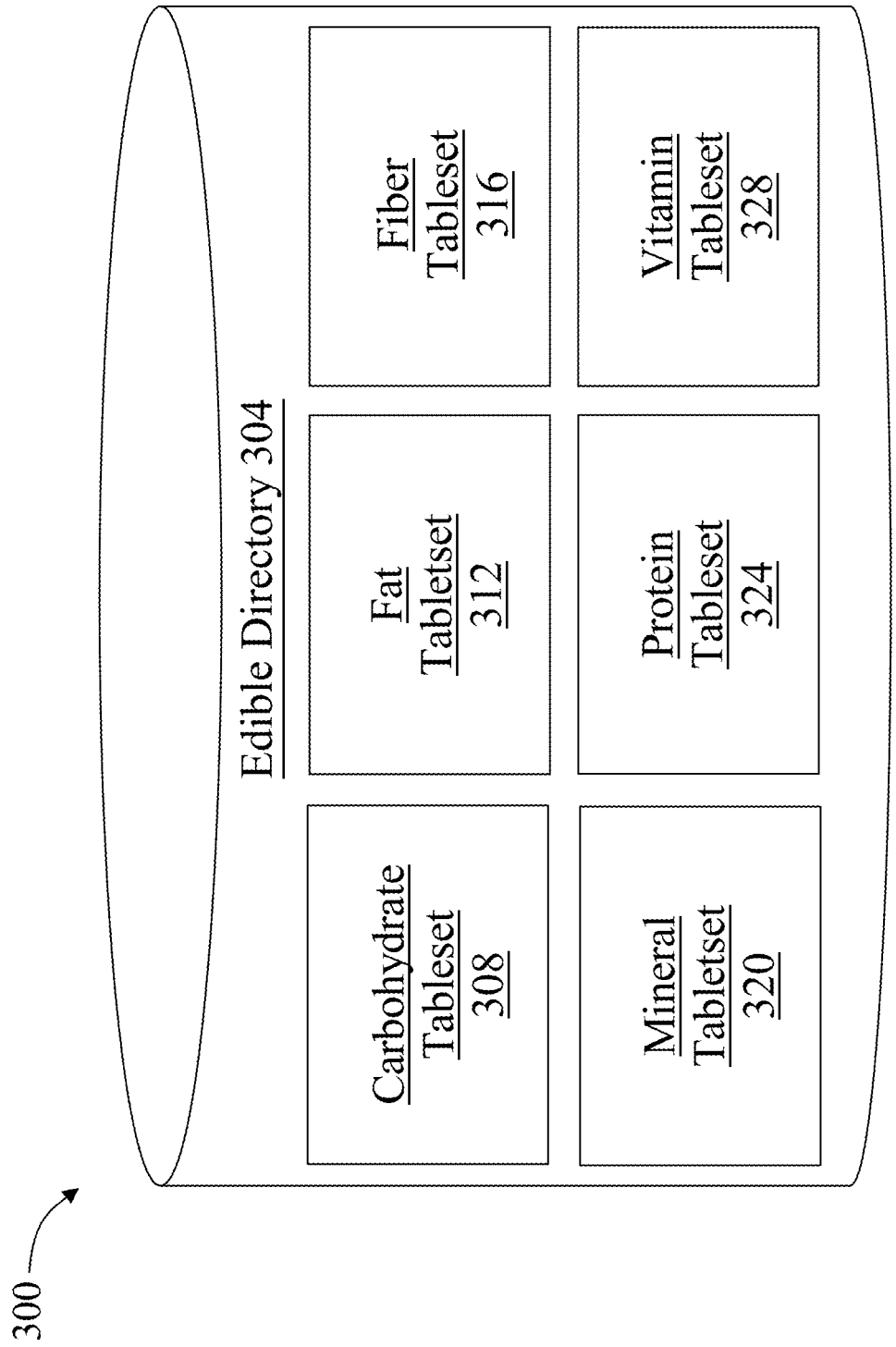
FIG. 3 is a block diagram of an exemplary embodiment of an edible directory according to an embodiment of the invention.

Now referring to FIG. 3, an exemplary embodiment 300 of an edible directory 304 according to an embodiment of the invention is illustrated. Edible directory 304 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 304 may alternatively or additionally be implemented using a distributed data storage protocol and/or data structure, such as a distributed hash table or the like. Edible directory 304 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 304 may include a carbohydrate tableset 308. Carbohydrate tableset 308 may relate to a nourishment composition of an edible with respect to the quantity and/or type of carbohydrates in the edible. As a non-limiting example, carbohydrate tableset 308 may include monosaccharides, disaccharides, oligosaccharides, polysaccharides, and the like thereof. Edible directory 304 may include a fat tableset 312. Fat tableset 312 may relate to a nourishment composition of an edible with respect to the quantity and/or type of esterified fatty acids in the edible. Fat tableset 312 may include, without limitation, triglycerides, monoglycerides, diglycerides, phospholipids, sterols, waxes, and free fatty acids. Edible directory 304 may include a fiber tableset 316. Fiber tableset 316 may relate to a nourishment composition of an edible with respect to the quantity and/or type of fiber in the edible. As a non-limiting example, fiber tableset 316 may include soluble fiber, such as beta-glucans, raw guar gum, psyllium, inulin, and the like thereof as well as insoluble fiber, such as wheat bran, cellulose, lignin, and the like thereof. Edible directory 304 may include a mineral tableset 320. Mineral tableset 320 may relate to a nourishment composition of an edible with respect to the quantity and/or type of minerals in the edible. As a non-limiting example, mineral tableset 320 may include calcium, phosphorous, magnesium, sodium, potassium, chloride, sulfur, iron, manganese, copper, iodine, zing, cobalt, fluoride, selenium, and the like thereof. Edible directory 304 may include a protein tableset 324. Protein tableset 324 may relate to a nourishment composition of an edible with respect to the quantity and/or type of proteins in the edible. As a non-limiting example, protein tableset 324 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 304 may include a vitamin tableset 328. Vitamin tableset 328 may relate to a nourishment composition of an edible with respect to the quantity and/or type of vitamins in the edible. As a non-limiting example, vitamin tableset 328 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
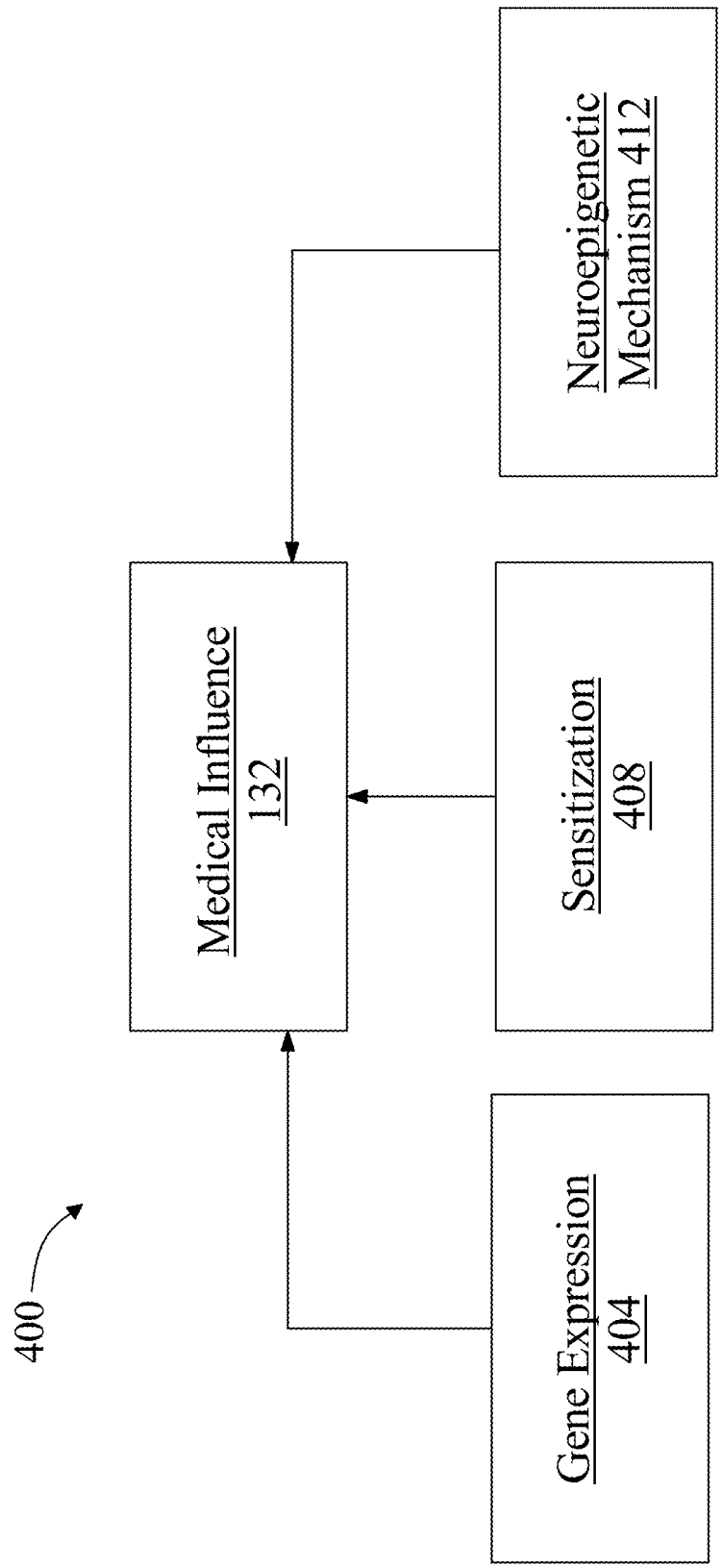
FIG. 4 is a block diagram of an exemplary embodiment of a medical influence according to an embodiment of the invention.

Referring now to FIG. 4, an exemplary embodiment of medical influence 132 is illustrated. Medical influence 132 may include a gene expression 404. As used in this disclosure a "gene expression" is an influence as a result of an altered production and/or expression of a gene and/or transcription factor. For example, and without limitation gene expression 404 may include alterations with transcription factor such as protein fosB, cyclic adenosine monophosphate response element binding protein, nuclear factor kappa B, and the like thereof. As a further non-limiting example gene expression 404 may include one or more altered productions of neurotransmitters such as dopamine, serotonin, glutamate, and the like thereof. As a further non-limiting example, gene expression 404 may include one or more altered productions and/or expressions of G9a, histone methyltransferase, nucleus accumbens D1-type medium spiny neurons, and the like thereof. Medical influence 132 may include a sensitization 408. As used in this disclosure a "sensitization" is an influence that causes a required increase of a particular sensation, neurotransmitter, and/or electrical signal to elucidate a particular response. For example, and without limitation, sensitization 408 may include requiring an elevated concentration of protein fosB to elucidate the response of an analgesic effect of opioids. As a further non-limiting example, sensitization 408 may include requiring an elevated electrical signal to be sent to the nucleus accumbens to elucidate a neurochemical release. Medical influence 132 may include neuroepigenetic mechanism 412. As used in this disclosure a "neuroepigenetic mechanism" is an influence on an individual's nervous system as a function of epigenetics. For example, and without limitation, neuroepigenetic mechanism may include one or more epigenetic modifications of neurons such as histone modifications, epigenetic methylation of DNA at CpG sites, epigenetic downregulation and/or upregulation of microRNAs that have particular target genes and the like thereof. As further non-limiting example, neuroepigenetic mechanism 412 may include upregulation of histone residues on the nucleus accumbens as a function of a drug exposure.

Figure 5:
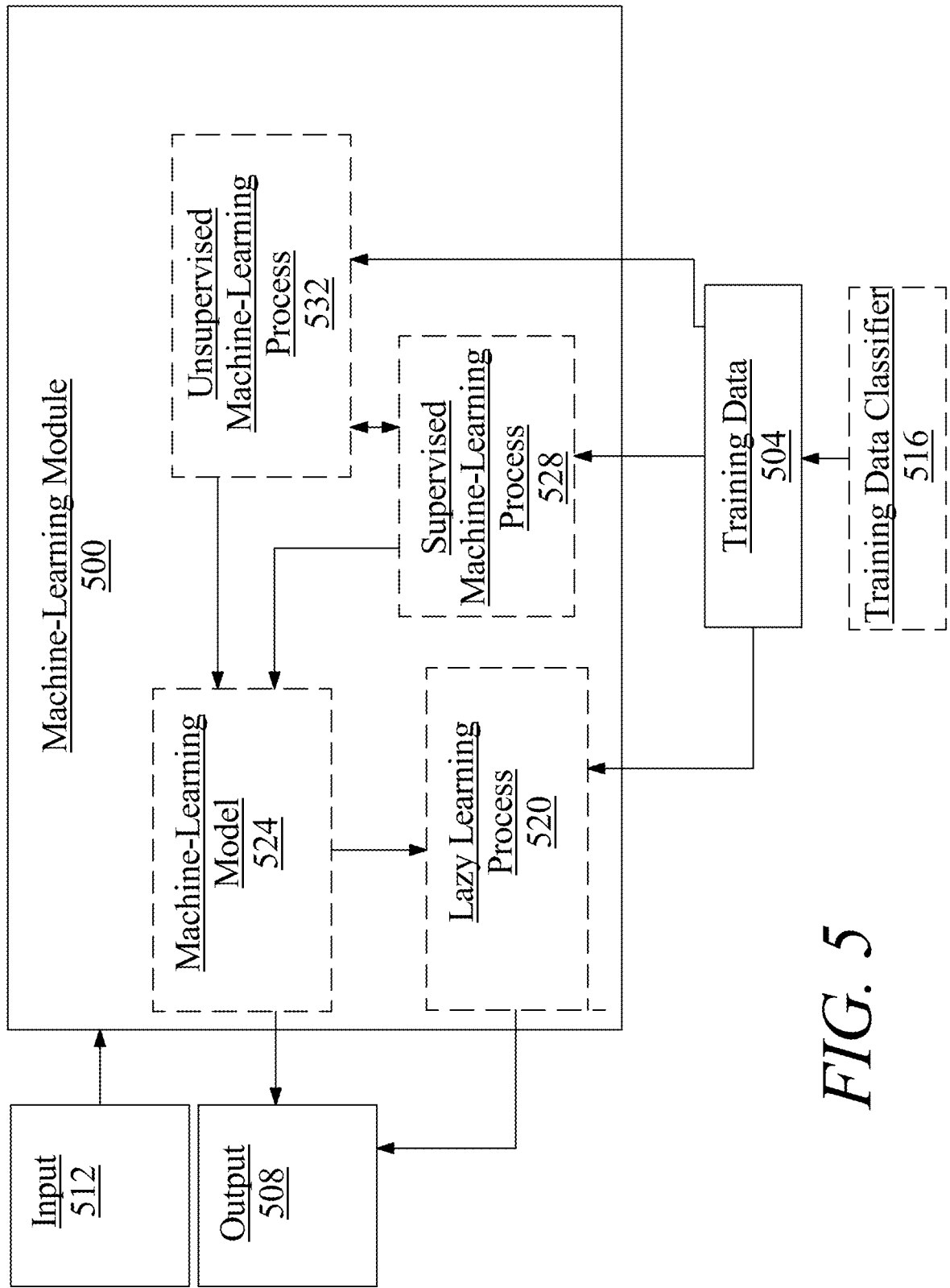
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example an input of a predictive signal and/or addiction element may output an addiction signature.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to sub-categories of predictive signals such as a high probability, average probability and/or low probability.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include predictive signals and/or addiction elements as described above as inputs, addiction signatures as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
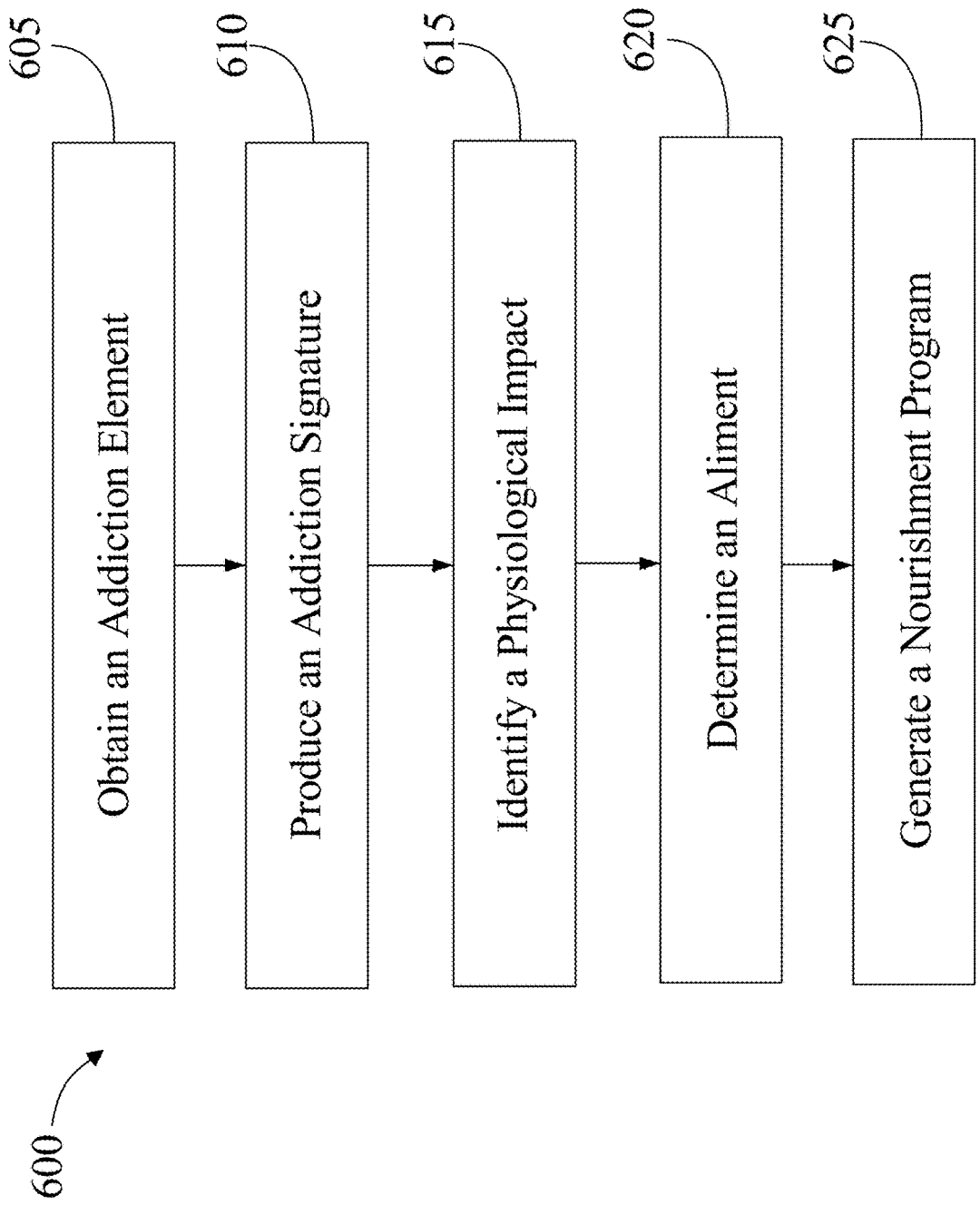
FIG. 6 is a process flow diagram illustrating an exemplary embodiment of a method of generating an addiction nourishment program.

Now referring to FIG. 6, an exemplary embodiment of a method 600 for generating an addiction nourishment program is illustrated. At step 605, a computing device 104 obtains an addiction element 108. Computing device 104 includes any of the computing device 104 as described above, in reference to FIGS. 1-5. Addiction element 108 includes any of addiction element 108 as described above, in reference to FIGS. 1-5.

Still referring to FIG. 6, at step 610, computing device 104 produces an addiction signature 112 as a function of addiction element 108. Addiction signature 112 includes any of the addiction signature 112 as described above, in reference to FIGS. 1-5. Computing device 104 produces addiction signature 112 by identifying a predictive signal 116. Predictive signal 116 includes any of the predictive signal 116 as described above, in reference to FIGS. 1-5. Predictive signal 116 is identified as a function of an addiction directory 120. Addiction directory 120 includes any of the addiction directory 120 as described above, in reference to FIGS. 1-5. Computing device 104 produces addiction signature 112 as a function of predictive signal 116 and addiction element 108 using a predictive machine-learning model 124.

Still referring to FIG. 6, at step 615, computing device 104 identifies a physiological impact 128 as a function of addiction signature 112. Physiological impact 128 includes any of the physiological impact 128 as described above, in reference to FIGS. 1-5. Computing device 104 identifies physiological impact 128 by receiving a medical influence 132. Medical influence 132 includes any of the medical influence 132 as described above, in reference to FIGS. 1-5. Computing device 104 identifies physiological impact 128 as a function of medical influence 132 and addiction signature 112 using a physiological machine-learning model 136.

Still referring to FIG. 6, at step 620, computing device 104 determines an edible 140 as a function of physiological impact 128. Edible 140 includes any of the edible 140 as described above, in reference to FIGS. 1-5.

Still referring to FIG. 6, at step 625, computing device 104 generates a nourishment program 144 as a function of edible 140. Nourishment program 144 includes any of the nourishment program 144 as described above, in reference to FIGS. 1-5. It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
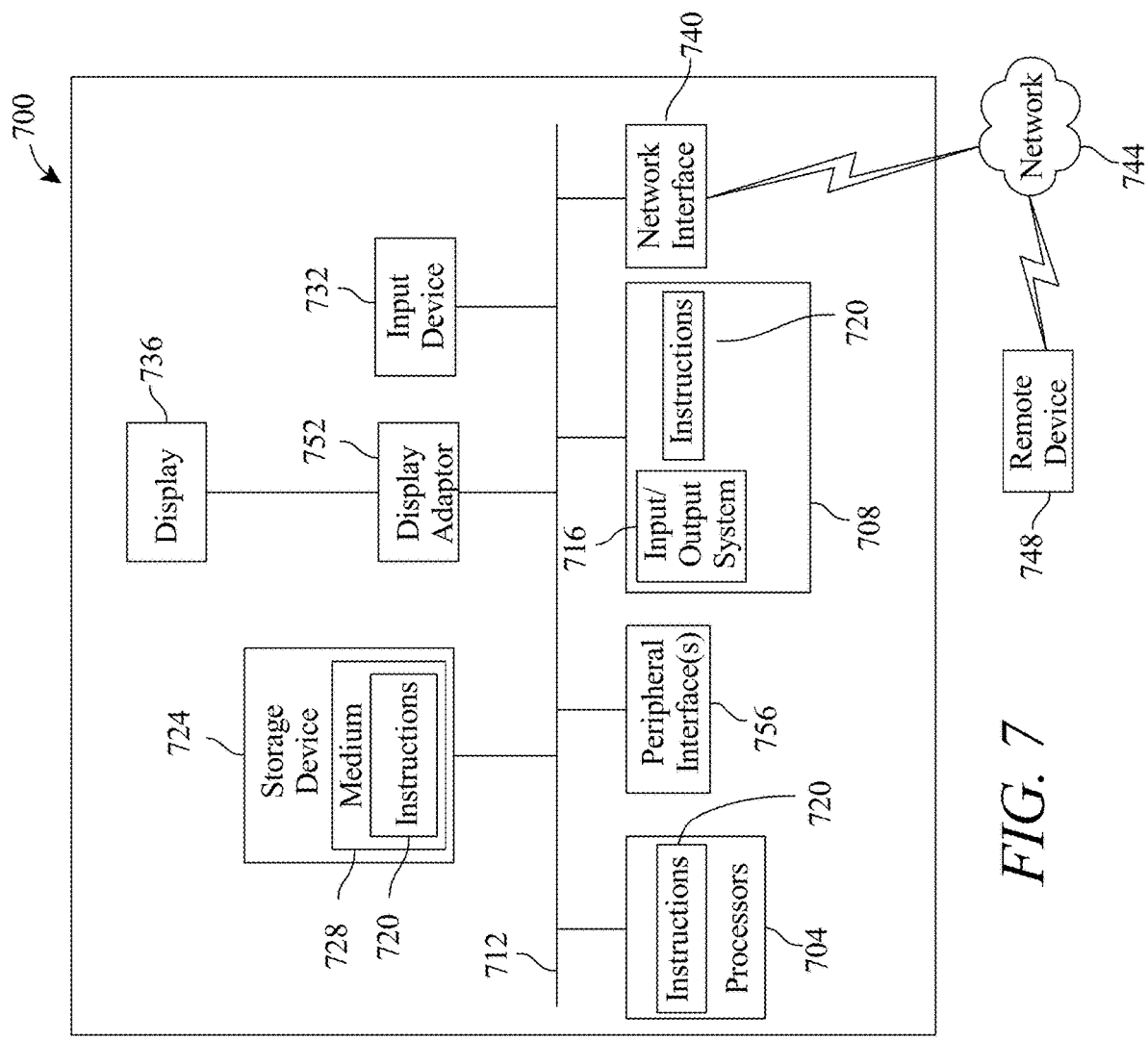
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating an addiction nourishment program, the system comprising:

a biological sampling device configured to collect a biological sample from an individual;

a computing device, the computing device configured to:
obtain an addiction element from the biological sample collected from the individual by the biological sampling device;
produce an addiction signature as a function of the addiction element, wherein producing the addiction signature further comprises:
identifying a predictive signal as a function of an addiction directory; and
producing the addiction signature as a function of the predictive signal and the addiction element, wherein predicting the addiction signature comprises:
generating a predictive machine-learning model;
transmitting, to a remote device, the predictive machine-learning model;
generating, by the remote device, an updated predictive machine-learning model by training the predictive machine-learning model utilizing a predictive training set, wherein the predictive training set correlates the predictive signal and the addiction element to the addiction signature;
transmitting, to the computing device, the updated predictive machine-learning model; and
producing the addiction signature using the updated predictive machine-learning model, wherein the predictive signal and the addiction element are provided to the updated predictive machine-learning model as inputs to output the addiction signature;
identify a physiological impact as a function of the addiction signature, wherein the physiological impact includes at least one psychological symptom, wherein identifying a physiological impact further comprises;
receiving a medical influence; and
identifying the physiological impact as a function of the medical influence and addiction signature using a physiological machine-learning model, wherein the physiological machine-learning model uses the output from the predictive machine-learning model as an input, and wherein the physiological machine-learning model is updated by incorporating a new medical influence that relates to a modified addiction signature;
determine an edible as a function of the physiological impact; and
generate a nourishment program as a function of the edible.

2. The system of claim 1, further comprising:
obtaining the addiction element, wherein obtaining the addiction element further includes:
receiving a medical assessment from an informed advisor; and
obtaining the addiction element as a function of the medical assessment.

3. The system of claim 1, wherein the addiction element includes a financial history input.

4. The system of claim 1, wherein producing the addiction signature includes determining a rehabilitation phase and producing the addiction signature as a function of the rehabilitation phase.

5. The system of claim 1, wherein producing the addiction signature includes determining an addiction dysfunction and producing the addiction signature as a function of the addiction dysfunction.

6. The system of claim 1, wherein receiving the medical influence includes:
obtaining a medical source; and
receiving the medical influence as a function of the medical source.

7. The system of claim 1, wherein the physiological impact includes a social symptom.

8. The system of claim 1, wherein determining the edible further comprises determining a withdrawal element and determining the edible as a function of the withdrawal element.

9. The system of claim 1, wherein determining the edible further comprises:
receiving a nourishment composition from an edible directory;
producing a nourishment demand as a function of the physiological impact; and
determining the edible as a function of the nourishment composition and the nourishment demand using an edible machine-learning model.

10. The system of claim 1, wherein generating the nourishment program further comprises:
receiving an addiction outcome; and
generating the nourishment program as a function of the addiction outcome using a nourishment machine-learning model.

11. A method for generating an addiction nourishment program, the method comprising:
obtaining an addiction element comprising a biological sample including nucleic acid collected from an individual from a biological sampling device;
producing, by a computing device, an addiction signature as a function of the addiction element, wherein producing the addiction signature further comprises:
identifying a predictive signal as a function of an addiction directory; and
producing the addiction signature as a function of the predictive signal and addiction element using a predictive machine-learning model, wherein predicting the addiction signature comprises:
generating, a predictive machine-learning model;
transmitting, to a remote device, the predictive machine-learning model;
generating, by the remote device, an updated predictive machine-learning model, by training the predictive machine-learning model utilizing a predictive training set, wherein the predictive training set correlates the predictive signal and the addiction element to the addiction signature;
transmitting, to the computing device, the updated predictive machine-learning model; and
producing the addiction signature using the updated predictive machine-learning model, wherein the predictive signal and the addiction element are provided to the updated predictive machine-learning model as inputs to output the addiction signature;
identifying, by the computing device, a physiological impact as a function of the addiction signature, wherein the physiological impact includes at least one psychological symptom, wherein identifying a physiological impact further comprises;
receiving a medical influence; and identifying the physiological impact as a function of the medical influence and addiction signature using a physiological machine-learning model, wherein the physiological machine-learning model uses the output from the predictive machine-learning model as an input and wherein the physiological machine-learning model is updated by incorporating a new medical influence that relates to a modified addiction signature;

determining, by the computing device, an edible as a function of the physiological impact; and generating, by the computing device, a nourishment program as a function of the edible.

12. The method of claim 11, wherein obtaining the addiction element includes:

receiving a medical assessment from an informed advisor; and obtaining the addiction element as a function of the medical assessment.

13. The method of claim 11, wherein the addiction element includes a financial history input.

14. The method of claim 11, wherein producing the addiction signature includes determining a rehabilitation phase and producing the addiction signature as a function of the rehabilitation phase.

15. The method of claim 11, wherein producing the addiction signature includes determining an addiction dysfunction and producing the addiction signature as a function of the addiction dysfunction.

16. The method of claim 11, wherein receiving the medical influence includes:

obtaining a medical source; and receiving the medical influence as a function of the medical source.

17. The method of claim 11, wherein the physiological impact includes a social symptom.

18. The method of claim 11, wherein determining the edible further comprises determining a withdrawal element and determining the edible as a function of the withdrawal element.

19. The method of claim 11, wherein determining the edible further comprises:

receiving a nourishment composition from an edible directory;

producing a nourishment demand as a function of the physiological impact; and determining the edible as a function of the nourishment composition and the nourishment demand using an edible machine-learning model.

20. The method of claim 11, wherein generating the nourishment program further comprises:

receiving an addiction outcome; and generating the nourishment program as a function of the addiction outcome using a nourishment machine-learning model.

* * * * *